US00PP11868P2

(12) United States Plant Patent
Zaiger et al.

(10) Patent No.: US PP11,868 P2
(45) Date of Patent: May 15, 2001

(54) PEACH TREE NAMED 'GLACIER'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/240,343

(22) Filed: Jan. 29, 1999

(51) Int. Cl.[7] ..... A01H 5/00
(52) U.S. Cl. ..... Plt./196
(58) Field of Search ..... Plt./196

*Primary Examiner*—Bruce R Campell
*Assistant Examiner*—Anne Marie Grünberg

(57) ABSTRACT

A new and distinct variety of peach tree (*Prunus persica*). The following features of the tree and its fruit are characterized with the tree budded on 'Nemaguard' rootstock (unpatented), grown on Handford Sandy loam soil with Storie Index rating 95, in USDA Hardiness Zone 9, near Modesto, Calif., with standard commercial fruit growing practices, such as, pruning, thinning, spraying, irrigation and fertilization. Its novelty consists of the following unique combination of features that are desirable in a new variety:

1. Regular and heavy production of fruit.
2. Fruit with large size and good firmness.
3. Fruit having an attractive red skin color.
4. Sweet, sub-acid fruit with excellent flavor and eating quality.
5. Fruit having firm, white flesh, with good storage and shipping qualities.
6. Fruit that has the ability to remain firm on the tree 7 to 10 days after maturity (shipping ripe).

1 Drawing Sheet

ORIGIN OF THE VARIETY

The present new variety of peach tree (*Prunus persica*) was originated by us in our experimental orchard located near Modesto, Calif., as an open pollinated seedling from a seedling of a cross between two seedlings with field identification Nos. 36RB243 and 103ED581. The maternal parent (36RB243) originated as an open pollinated seedling from a cross between a seedling with field identification No. 16EA132 and 'Amparo Peach' (U.S. Plant Pat. No. 6,472. The seedling (16EA132) originated as an open pollinated seedling from a peach of unknown parentage. The pollen parent (103ED581) originated as an open pollinated seedling between a cross of two seedlings with field identification Nos. 23EA150 and 54G51. The seedling (23EA150) originated from an open pollinated 'O'Henry' Peach (U.S. Plant Pat. No. 2,964) seed. The seedling (54G51) originated from an open pollinated peach seedling from a peach of unknown parentage. We grew and maintained a large group of these seedlings, growing on their own root, during which time one such seedling, which is of the present variety, being especially desirable for its tree and fruit characteristics described below, was selected for asexual reproduction and commercialization.

ASEXUAL REPRODUCTION OF THE VARIETY

Asexual reproduction of the new and distinct variety of peach tree was by budding to 'Nemaguard' rootstock (unpatented), as performed by us in our experimental orchard located near Modesto, Calif., and shows that reproductions run true to the original tree and all characteristics of the tree and the fruit are established and transmitted through succeeding asexual propagations.

SUMMARY OF THE VARIETY

The new and distinct variety of peach tree is of large size, vigorous, upright growth, and is a productive and regular bearer of large size, white flesh freestone fruit that has good storage and shipping qualities. The fruit is further characterized by its attractive red skin color, firm flesh, sweet, sub-acid flavor and excellent eating quality, its ability to remain firm on the tree 7 to 10 days after maturity and, in comparison to 'Summer Sweet' Peach (U.S. Plant Pat. No. 8,070), which it resembles in firmness and flavor, the new variety is approximately 7 days later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size*.—Large. Tree height controlled by selective pruning 12 to 14 feet in height and 12 to 14 feet in width for economical harvesting of fruit.

*Vigor*.—Vigorous. Tree growth of 5 to 7 feet in height and 4 to 6 feet in width the first growing season. Pruned, during the first dormant season to 4 to 5 feet in height when primary branches are selected for desirable scaffolds and to promote proper tree growth for secondary scaffolds to be selected in second dormant season.

*Form.*—Upright.

*Productivity.*—Productive, producing 1½ to several times the number of fruit for desired crop load. Fruit is thinned and spaced to the desired number to develop marketable size fruit.

*Bearer.*—Regular, has produced adequate fruit set for 5 consecutive years.

*Density.*—Medium dense, usually pruned to vase shape by removing small limbs and twigs from center of tree to allow for more sunlight to enhance fruit color and Brix.

*Hardiness.*—Tested in USDA Hardiness Zone 9. Estimated chilling requirement 750 to 850 hours below 45° F.

Trunk:

*Size.*—Medium stocky. Circumference of 22 inches at 12 inches above the ground on an 8 year old tree. Varies with soil type, climatic conditions and cultural practices.

*Texture.*—Medium shaggy.

*Color.*—Brown to soot brown (5-E-5) to (5-F-6).

Branches:

*Size.*—Medium. Circumference averages 8½ inches at 30 inches above the ground.

*Texture.*—Smooth to medium rough. Roughness increases with age of branch.

*Lenticels.*—Numerous. Average number of 60 in a 4 square inch section. Small to medium in size, 11/64 inch in length, 3/64 inch in width. Size increases as branches become larger. Color varies from fox red to reddish brown (8-D-7) to (8-D-6).

*Color.*—Light brown to brown (5-D-5) to (5-E-7). Color gets darker brown with age of branch.

Leaves:

*Size.*—Large. Average length 6⅜ inches. Average width 1⅝ inches.

*Form.*—Lanceolate. Pointed.

*Margin.*—Crenate.

*Thickness.*—Medium.

*Surface.*—Smooth.

*Petiole.*—Medium. Average length 7/16 inch. Average width 3/64 inch. Grooved longitudinally. Color varies from green to deep green (28-D-8) to (29-D-8).

*Glands.*—Reniform. Medium in size, average diameter 3/64 inch. Number varies from 2 to 5. Average No. 3. Color—grayish yellow to grayish green (1-B-7) to (1-C-6). Located on base of leaf blade and upper portion of petiole.

*Color.*—Upper surface — green to dark green (29-F-6) to (29-F-8). Lower surface — grayish green to deep green (29-E-7) to (29-E-8).

Flower buds:

*Size.*—Medium to large. Average length ⅗ inch. Average diameter ⅖ inch, 4 days before full bloom.

*Form.*—Plump.

*Pubescence.*—Pubescent.

*Color.*—Pink (11-A-2).

Flowers:

*Size.*—Large, showy. 1½ to 1⅝ inches in diameter.

*Petal.*—Nunber—5. Obovate, edges vary from smooth to slightly scalloped. Average length 11/16 inch. Average width 9/16 inch.

*Sepals.*—Number—5. Alternately arranged to petals. Obovate, with smooth edges. Pubescent. Average length ⅕ inch. Average width ⅕ inch. Color—violet brown to garnet brown (11-E-6) to (11-E-8), except along outer edges, which are wax yellow to olive yellow (3-B-5) to (3-C-5).

*Pollen.*—Present, self-fertile.

*Stamens.*—Number of stamens varies from 40 to 45. Average length 17/37 inch. Filament color—white (1-A-1), turning pink with age of bloom. Anther color—cardinal red (10-D-8).

*Pistil.*—Usually one. Pubescent. Average length 9/20 inch. Color—yellowish-white to pastel yellow (1-A-2) to (1-A-4).

*Aroma.*—None.

*Color.*—Pink to light pink (11-A-2) to (11-A-3). Color fades with age of bloom.

*Blooming period.*—Date of First Bloom: Feb. 15, 1997. Date of Last Bloom: Feb. 23, 1997. Varies slightly with climatic conditions.

Fruit:

*Maturity when described.*—Shipping ripe.

*Date of first picking.*—Jul. 12, 1997.

*Date of last picking.*—Jul. 17, 1997. Varies slightly with climatic conditions.

*Size.*—Large. Average diameter axially—2¾ to 3 inches. Average transversely in suture plane—2⅞ to 3 inches. Average weight 191 grams, varies from 178 to 200. Varies with number of fruit per tree, soil type, climatic conditions and cultural practices.

*Form.*—Nearly globose, slightly flattened at stem end.

*Suture.*—Shallow, extends from base to apex.

*Ventral surface.*—Usually rounded, some fruit slightly lipped.

*Apex.*—Usually rounded, varies from slight tip to slight depression.

*Base.*—Retuse.

*Cavity.*—Slightly elongated in suture plane. Average depth 7/16 inch. Average breadth 1 inch.

Stem:

*Size.*—Average length ¼ to 9/32 inch. Average diameter ⅛ inch. Enlarged at point of fruit attachment.

*Color.*—Olive gray to olive yellow (2-D-4) to (2-D-6).

Flesh:

*Ripens.*—Evenly.

*Texture.*—Firm.

*Fibers.*—Few, small and tender.

*Aroma.*—Moderate.

*Amygdalin.*—Undetected.

*Juice.*—Moderate, mild, sub-acid, sweet, enhances flavor. Average Brix 12.0°.

*Eating quality.*—Excellent.

*Flavor.*—Excellent, mild, sweet, sub-acid.

*Color.*—White to pinkish white near pit cavity (11-A-1) to (11-A-2). Pit cavity varies from pastel pink to dull red (11-A-4) to (11-B-6). Bleeding of pinkish red from pit cavity into flesh, heavier toward the apex.

Skin:

*Thickness.*—Medium.

*Texture.*—Medium, tenacious to the flesh.

*Down.*—Moderate amount. Medium length.

*Tendency to crack.*—None.

*Color.*—White to pinkish white ground color (9-A-1) to (9-A-2). Nearly overspread with pale red to light red (9-A-4) to (9-A-6). Fruit exposed to sunlight have a higher degree of enhanced red skin color.

Stone:

*Type*.—Freestone.

*Size*.—Large. Average length 1⅜ inches. Average width 1 inch. Average thickness ¾ inch.

*From*.—Oval to ovoid.

*Base*.—Usually straight, varies from straight to rounded.

*Apex*.—Cuspidate.

*Surface*.—Irregularly furrowed toward apex, pitted toward base, pit cavities vary from round to elongated.

*Sides*.—Equal to unequal. Some stones have one side slightly larger, extending farther from the suture plane.

*Tendency to split*.—None.

*Color*.—Reddish brown to brown (9-E-7) to (10-E-7).

Use: Dessert.

*Market*.—Local and long distance.

Storage quality: Good, fruit holds firm for two weeks in cold storage with no internal breakdown of flesh or appreciable loss of eating quality.

Shipping quality: Good, picking and packing of fruit gave minimal bruising or scarring of flesh or skin.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, characterized by its large size, vigorous and upright growth; being a productive and regular bearer of large size fruit with firm, white flesh, sweet sub-acid flavor and excellent eating quality; the fruit is further characterized by its good storage and shipping quality, its ability to remain firm on the tree 7 to 10 days after maturity; and, in comparison to the 'Summer Sweet' Peach (U.S. Plant Pat. No. 8,070), the new variety is approximately 7 days later in maturity.

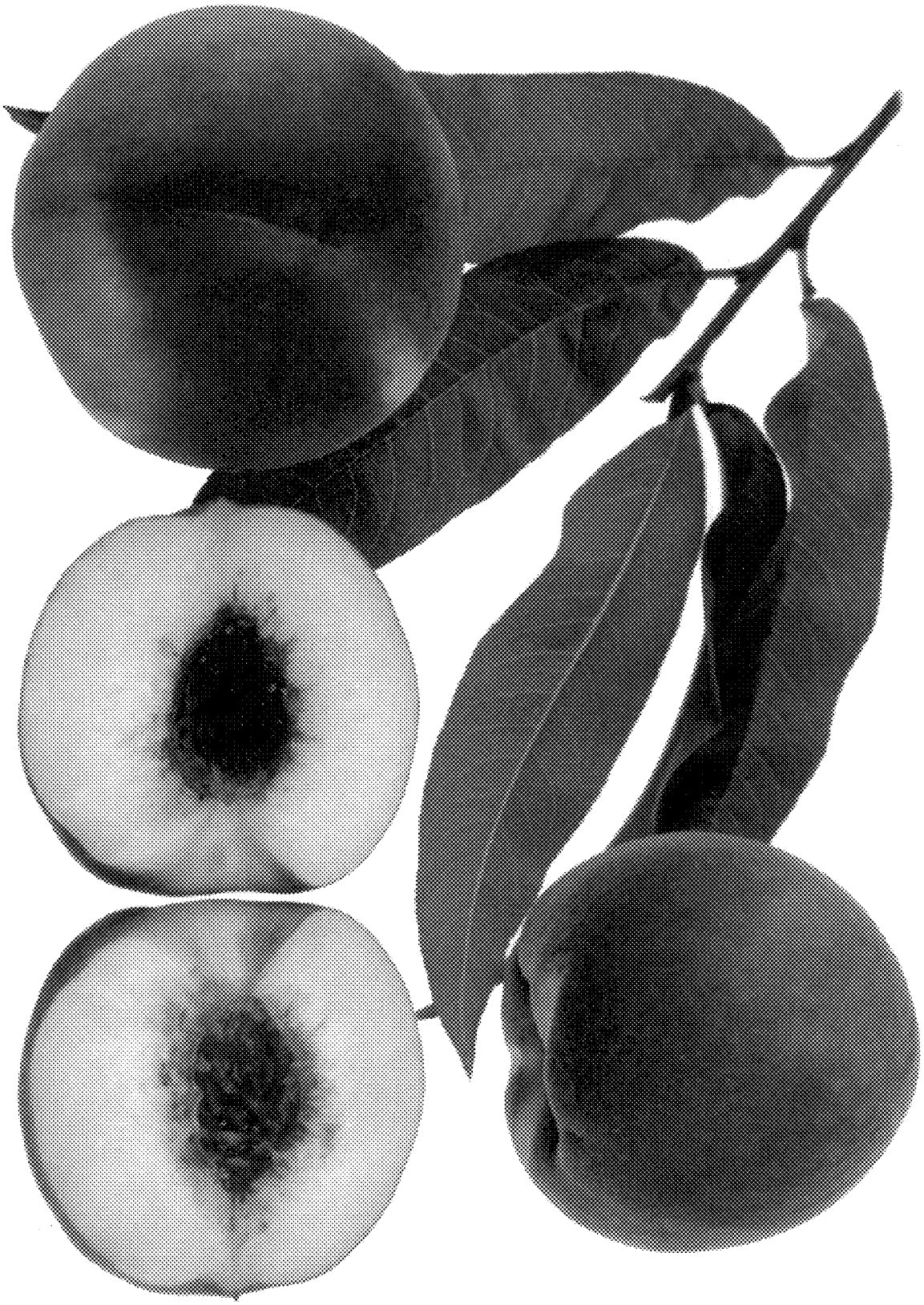

* * * * *